US011033347B2

(12) United States Patent
Hiratsuka et al.

(10) Patent No.: US 11,033,347 B2
(45) Date of Patent: *Jun. 15, 2021

(54) SURGICAL SYSTEM (71) Applicant: KAWASAKI JUKOGYO KABUSHIKI KAISHA, Kobe (JP)

(72) Inventors: Mitsuichi Hiratsuka, Kobe (JP); Tetsuya Nakanishi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 383 days.

This patent is subject to a terminal disclaimer.

(21) Appl. No.: 16/093,699

(22) PCT Filed: Apr. 12, 2017

(86) PCT No.: PCT/JP2017/015020
§ 371 (c)(1),
(2) Date: Oct. 15, 2018

(87) PCT Pub. No.: WO2017/179629
PCT Pub. Date: Oct. 19, 2017

(65) Prior Publication Data
US 2019/0133704 A1 May 9, 2019

(30) Foreign Application Priority Data

Apr. 15, 2016 (JP) .............................. JP2016-081856

(51) Int. Cl.
*A61B 34/37* (2016.01)
*B25J 3/00* (2006.01)
(Continued)

(52) U.S. Cl.
CPC .............. *A61B 34/37* (2016.02); *A61B 90/06* (2016.02); *A61B 90/08* (2016.02); *B25J 3/00* (2013.01);
(Continued)

(58) Field of Classification Search
CPC ......... G06T 7/0012; G06T 2207/10056; G06T 2207/30004; G06T 1/0014; A61B 34/20;
(Continued)

(56) References Cited

U.S. PATENT DOCUMENTS 6,723,106 B1    4/2004  Charles et al.
7,373,219 B2 *  5/2008  Nowlin ................. B25J 9/1689
                                          700/245
(Continued)

FOREIGN PATENT DOCUMENTS

CN      101160104 A      4/2008
JP      2002-530209 A    9/2002
(Continued)

OTHER PUBLICATIONS

Yue et al., Design and development of simulation system for minimally invasive surgery robot, 2014, IEEE, p. 825-829 (Year: 2014).*

(Continued)

*Primary Examiner* — McDieunel Marc
(74) *Attorney, Agent, or Firm* — Oliff PLC (57) ABSTRACT

A surgical system capable of securing a large movable range of a tip end of a surgical instrument even when the surgical instrument is inserted into a narrow region. One example of the surgical system includes: a manipulator; a surgical instrument including a shaft coupled to a tip end portion of the manipulator; a manipulation input portion to which an operator inputs a command regarding a position and posture of the surgical instrument; a control apparatus configured to control an operation of the manipulator based on the command input to the manipulation input portion; and a motion center position setting portion configured to set a desired position as a motion center position of the surgical instru- (Continued)

ment in the control apparatus, the desired position being located in an inner part under a body surface of the patient.

10 Claims, 7 Drawing Sheets

(51) Int. Cl.
*A61B 90/00* (2016.01)
*A61B 34/30* (2016.01)

(52) U.S. Cl.
CPC ... *A61B 2034/301* (2016.02); *A61B 2034/302* (2016.02); *A61B 2090/061* (2016.02); *A61B 2090/067* (2016.02); *A61B 2090/0807* (2016.02)

(58) Field of Classification Search
CPC ... A61B 34/10; A61B 2034/105; A61B 34/35; A61B 90/37; A61B 34/25; A61B 34/37; A61B 34/30; A61B 17/29; A61B 34/00; A61B 34/70; A61B 2034/107; A61B 2034/301; A61B 90/361; A61B 2034/302; A61B 2090/067; A61B 17/0281; A61B 17/34; A61B 1/00048; A61B 1/00149; A61B 1/00188; A61B 1/00193; A61B 1/042; A61B 2034/2055; A61B 2034/742; A61B 2090/061; A61B 2090/062; A61B 2090/064; A61B 2090/0807; A61B 2090/502; A61B 2090/506; A61B 34/32; A61B 34/74; A61B 90/06; A61B 90/08; A61B 90/13; G16H 40/67; B25J 9/1689; B25J 13/08; B25J 15/0019; B25J 19/02; B25J 9/1676; B25J 13/088; B25J 3/00; A61M 2205/50; G05B 2219/45083; G05B 2219/40418; G05B 2219/39442; Y10S 901/36

See application file for complete search history.

(56) References Cited

U.S. PATENT DOCUMENTS

| | | | |
|---|---|---|---|
| 7,607,440 B2* | 10/2009 | Coste-Maniere | A61B 34/70 128/898 |
| 9,259,280 B2* | 2/2016 | Au | A61B 34/37 |
| 2006/0142657 A1 | 6/2006 | Quaid et al. | |
| 2007/0293734 A1* | 12/2007 | Coste-Maniere | A61B 34/35 600/300 |
| 2010/0094312 A1 | 4/2010 | Ruiz Morales et al. | |
| 2013/0012930 A1* | 1/2013 | Ruiz Morales | A61B 34/35 606/1 |
| 2014/0052153 A1 | 2/2014 | Griffiths et al. | |
| 2014/0350572 A1 | 11/2014 | Elhawary et al. | |
| 2015/0202015 A1 | 7/2015 | Elhawary et al. | |
| 2016/0100898 A1 | 4/2016 | Jinno et al. | |
| 2016/0339586 A1 | 11/2016 | Komuro et al. | |
| 2019/0083185 A1* | 3/2019 | Smaby | A61B 34/70 |
| 2019/0388168 A1* | 12/2019 | Itkowitz | A61B 34/74 |
| 2020/0368915 A1* | 11/2020 | Itkowitz | B25J 9/1666 |

FOREIGN PATENT DOCUMENTS

| | | |
|---|---|---|
| JP | 2012-254303 A | 12/2012 |
| JP | 2015-502814 A | 1/2015 |
| JP | 2015-524309 A | 8/2015 |
| WO | 2006/091494 A1 | 8/2006 |
| WO | 2015/125649 A1 | 8/2015 |

OTHER PUBLICATIONS

Staub et al., Autonomous High Precision Positioning of Surgical Instruments in Robot-Assisted Minimally Invasive Surgery under Visual Guidance, 2010, IEEE, p. 64-69 (Year: 2010).*

Trejos et al., Port Placement for Endoscopic Cardiac Surgery Based on Robot Dexterity Optimization, 2005, IEEE, p. 912-917 (Year: 2005).*

Hagin et al., Telemanipulator for remote minimally invasive surgery, 2008, IEEE, p. 28-38 (Year: 2008).*

* cited by examiner

SURGICAL SYSTEM

TECHNICAL FIELD

The present invention relates to a surgical system.

BACKGROUND ART

A system including a manipulator used in surgery is conventionally known (see PTLs 1 and 2, for example).

In such system, a surgical instrument is attached to a tip end portion of the manipulator (arm). The surgical instrument includes a long and thin rod-shaped shaft. A treatment tool, such as forceps, is attached to a tip end of the shaft and is inserted into a body of a patient through an incised part of the patient. The manipulator is controlled by remote control of an operator. Thus, the position and posture of the surgical instrument can be changed.

CITATION LIST

Patent Literature

PTL 1: Published Japanese Translation of PCT Application No. 2002-530209
PTL 2: Published Japanese Translation of PCT Application No. 2015-502814

SUMMARY OF INVENTION

Technical Problem

According to the above conventional system, a motion center position of the surgical instrument when the position and posture of the surgical instrument is changed is located on a body surface of the patient or in the vicinity of the body surface. Therefore, for example, in thoracic surgery, when the surgical instrument is inserted between bones, such as ribs, the surgical instrument is manipulated such that the shaft of the surgical instrument does not contact the bones during the surgery. On this account, a movable range of a tip end of the surgical instrument is small, and this makes it difficult to perform the surgery.

The present invention was made to solve the above problem, and an object of the present invention is to provide a surgical system capable of securing a large movable range of a tip end of a surgical instrument even when the surgical instrument is inserted into a narrow region, for example, a region between bones, such as ribs.

Solution to Problem

To achieve the above object, a surgical system according to an aspect of the present invention includes: a manipulator configured such that a tip end portion thereof moves relative to a base end portion thereof in a three-dimensional space; a surgical instrument including a rod-shaped shaft coupled to the tip end portion of the manipulator and a treatment tool provided at a tip end portion of the shaft; a manipulation input portion to which an operator inputs a command regarding a position and posture of the surgical instrument; a control apparatus configured to control an operation of the manipulator based on the command input to the manipulation input portion; and a motion center position setting portion configured to set a desired position in the control apparatus as a motion center position of the surgical instrument inserted into an incised part of a patient, the desired position being located in an inner part under a body surface of the patient, wherein the control apparatus is configured to control the operation of the manipulator such that in a case where the control apparatus controls the operation of the manipulator based on the command, input to the manipulation input portion, after the surgical instrument is inserted into a body of the patient through the incised part, and the surgical instrument is arranged with the shaft passing through the motion center position, the position and posture of the surgical instrument are changed while maintaining a state where the shaft is located at the motion center position.

Advantageous Effects of Invention

The present invention is configured as explained above and has an effect of being able to provide a surgical system capable of securing a large movable range of a tip end of a surgical instrument even when the surgical instrument is inserted into a narrow region, for example, a region between bones, such as ribs.

DESCRIPTION OF EMBODIMENTS

A surgical system according to an aspect of the present invention includes: a manipulator configured such that a tip end portion thereof moves relative to a base end portion thereof in a three-dimensional space; a surgical instrument including a rod-shaped shaft coupled to the tip end portion of the manipulator and a treatment tool provided at a tip end portion of the shaft; a manipulation input portion to which an operator inputs a command regarding a position and posture of the surgical instrument; a control apparatus configured to control an operation of the manipulator based on the command input to the manipulation input portion; and a motion center position setting portion configured to set a desired position in the control apparatus as a motion center position of the surgical instrument inserted into an incised part of a patient, the desired position being located in an inner part under a body surface of the patient, wherein the control apparatus is configured to control the operation of the manipulator such that in a case where the control apparatus controls the operation of the manipulator based on the command, input to the manipulation input portion, after the surgical instrument is inserted into a body of the patient through the incised part, and the surgical instrument is arranged with the shaft passing through the motion center position, the position and posture of the surgical instrument are changed while maintaining a state where the shaft is located at the motion center position.

According to this configuration, the motion center position of the surgical instrument is set in (the inner part of) the body of the patient, instead of the body surface of the patient or near the body surface of the patient. With this, even when the surgical instrument is inserted into a narrow region, for example, a region between bones, such as ribs, a large movable range of the tip end of the surgical instrument can be secured. Thus, surgery is easily performed.

The motion center position setting portion may include a motion center position setting manipulation portion configured to, when the surgical instrument is inserted into the body of the patient through the incised part, and a predetermined reference point of the surgical instrument is located at the desired position in the body, perform an operation of setting the position as the motion center position in the control apparatus.

The surgical system may further include: an initial incised position setting portion configured to set a position of the incised part on the body surface of the patient as an initial incised position in the control apparatus; and a warning device configured to output a warning to the operator when the shaft is displaced from the initial incised position, and a predetermined condition is satisfied in a case where the control apparatus controls the operation of the manipulator after the surgical instrument is inserted into the body of the patient through the incised part, and the surgical instrument is arranged with the shaft passing through the motion center position. According to this configuration, by outputting the warning to the operator, the position of the incised part can be prevented from largely moving during surgery, which is preferable for the patient.

The motion center position setting portion may include: an initial incised position setting portion configured to set a position of the incised part on the body surface of the patient as an initial incised position in the control apparatus; and a calculating portion configured to calculate a position located away from the initial incised position by a predetermined distance in a predetermined direction and set the position as the motion center position in the control apparatus.

The surgical system may further include a warning device configured to output a warning to the operator when the shaft is displaced from the initial incised position, and a predetermined condition is satisfied in a case where the control apparatus controls the operation of the manipulator after the surgical instrument is inserted into the body of the patient through the incised part, and the surgical instrument is arranged with the shaft passing through the motion center position. According to this configuration, by outputting the warning to the operator, the position of the incised part can be prevented from largely moving during surgery, which is preferable for the patient.

The predetermined condition may be a condition in which a distance between the initial incised position and a position located away from the motion center position on a central axis of the current shaft by a distance between the initial incised position and the motion center position is not less than a predetermined value. In this case, it can be said that the predetermined condition is a condition in which an approximate value is not less than a predetermined value, the approximate value being calculated as an approximate value of a distance between a center position of the current incised part and the initial incised position.

The predetermined condition may be a condition in which a distance between the initial incised position and an intersecting position is not less than a predetermined value, the intersecting position being calculated as a position where a central axis of the current shaft intersects with a flat plane perpendicular to a vector, the vector passing through the initial incised position and extending from the motion center position toward the initial incised position. In this case, it can be said that the predetermined condition is a condition in which an approximate value is not less than a predetermined value, the approximate value being calculated as an approximate value of a distance between a center position of the current incised part and the initial incised position.

The initial incised position setting portion may include an initial incised position setting manipulation portion configured to, when the surgical instrument is inserted into the body of the patient through the incised part, and a predetermined reference point of the surgical instrument is located at a position of the incised part on the body surface of the patient, perform an operation of setting the position as the initial incised position in the control apparatus.

The surgical system may further include a warning device configured to output a warning to the operator when an angle formed by a vector indicating a direction of a central axis of the shaft when the motion center position is set and a vector indicating a direction of the central axis of the current shaft is not less than a predetermined angle in a case where the control apparatus controls the operation of the manipulator after the surgical instrument is inserted into the body of the patient through the incised part, and the surgical instrument is arranged with the shaft passing through the motion center position. According to this configuration, by outputting the warning to the operator, the position of the incised part can be prevented from largely moving during surgery, which is preferable for the patient.

The motion center position may be defined between adjacent bones in the body of the patient.

Hereinafter, a preferred embodiment will be explained with reference to the drawings. In the following explanations and the drawings, the same reference signs are used for the same or corresponding components, and a repetition of the same explanation is avoided. Further, the present invention is not limited to the embodiment below.

EMBODIMENT

Summary of Surgical System

Figure 1:
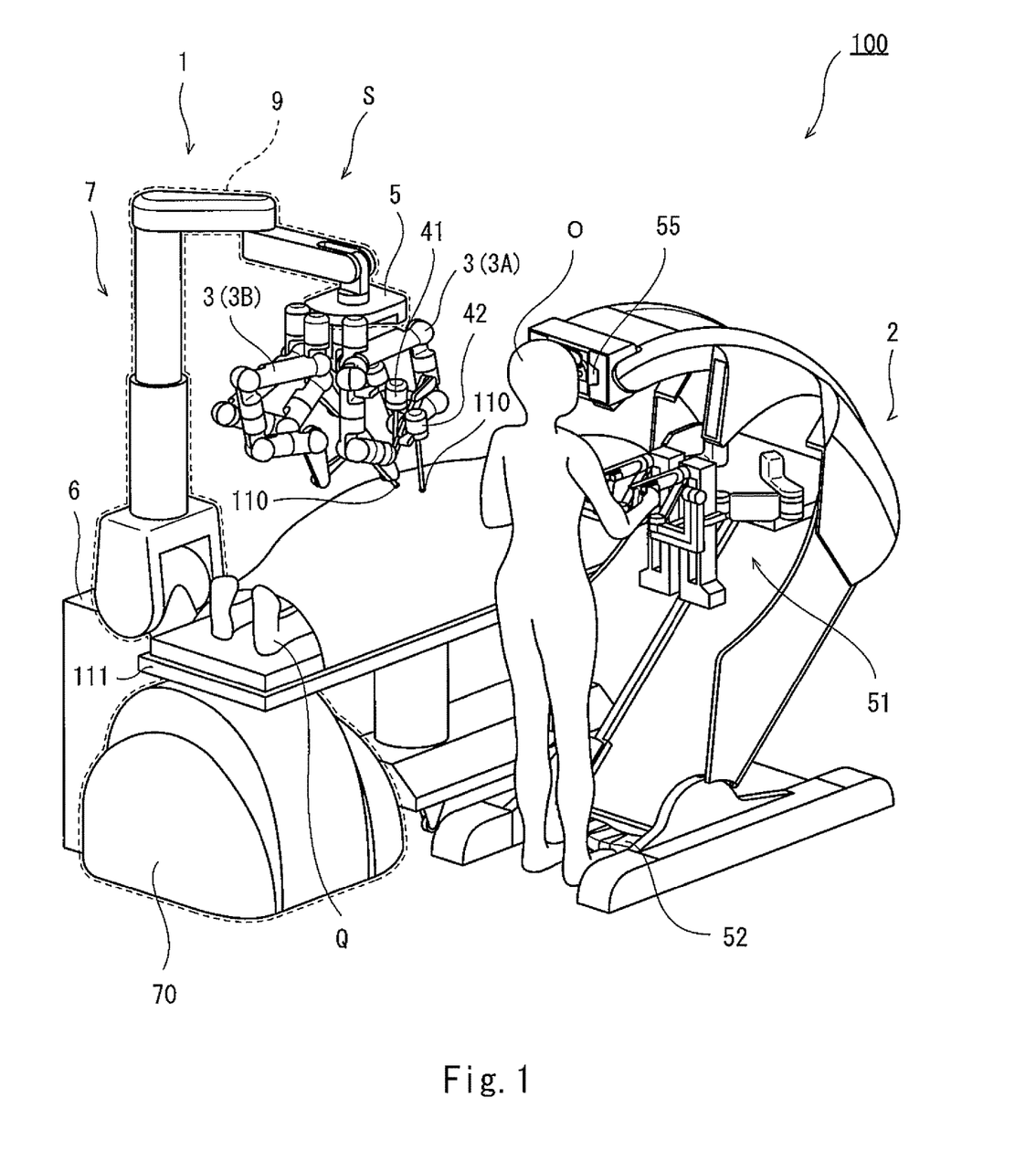
FIG. 1 is a schematic diagram showing one example of an entire configuration of a surgical system according to an embodiment of the present invention.
Figure 2:
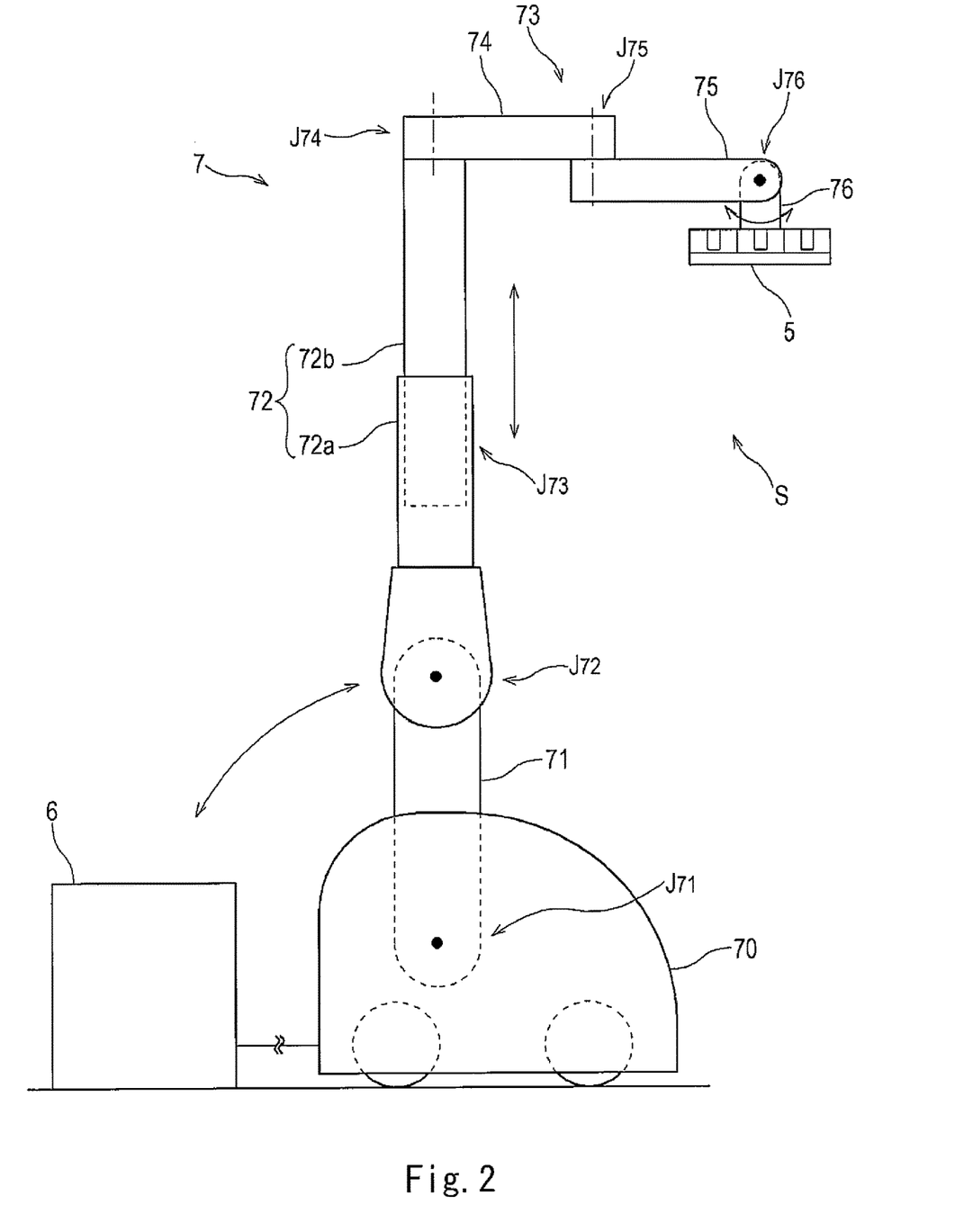
FIG. 2 is a side view showing one example of the configuration of a positioner of a patient-side apparatus.
Figure 3:
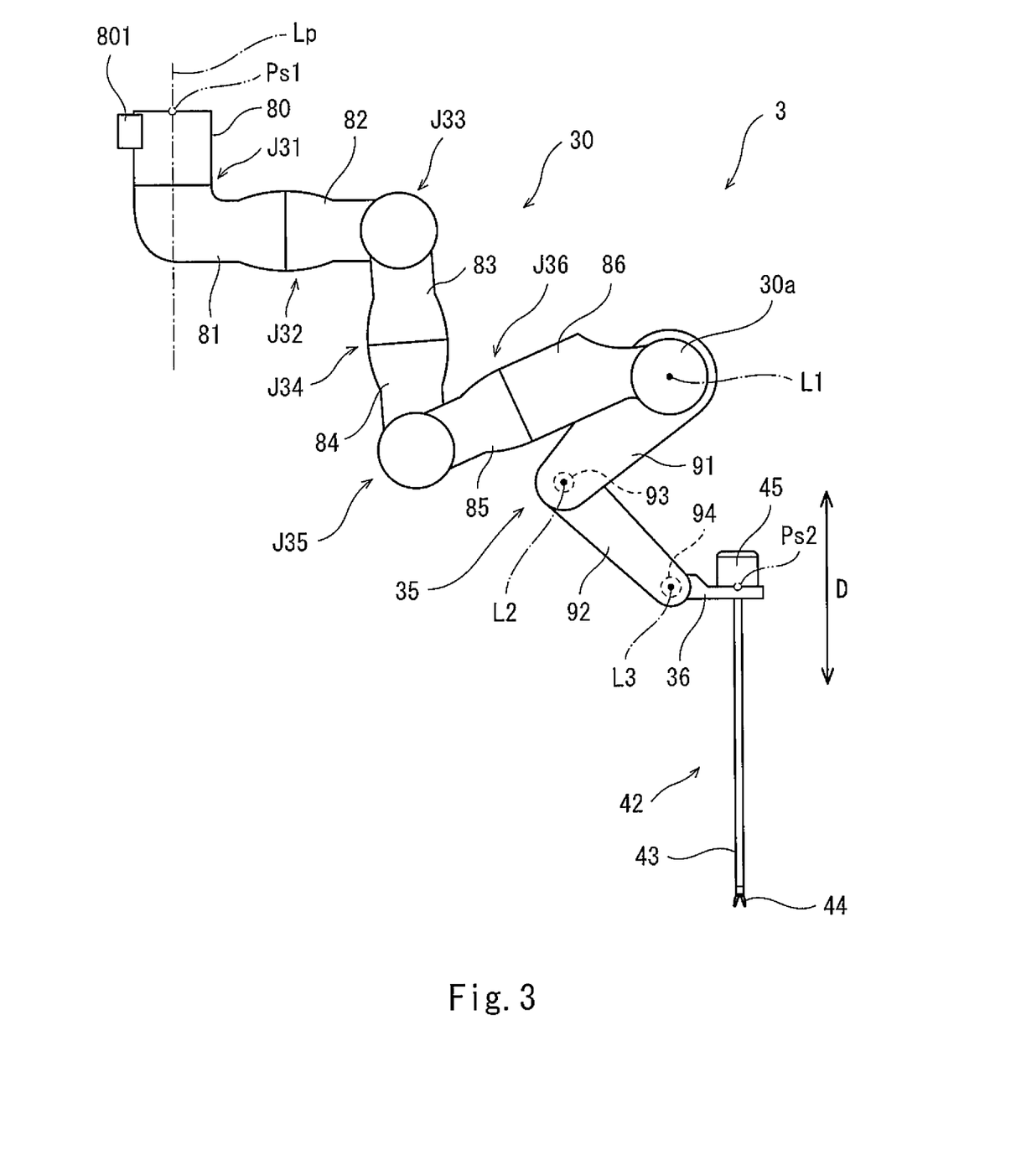
FIG. 3 is a schematic diagram showing one example of the configuration of a manipulator (arm) to which a surgical instrument of the patient-side apparatus is attached.
Figure 4:
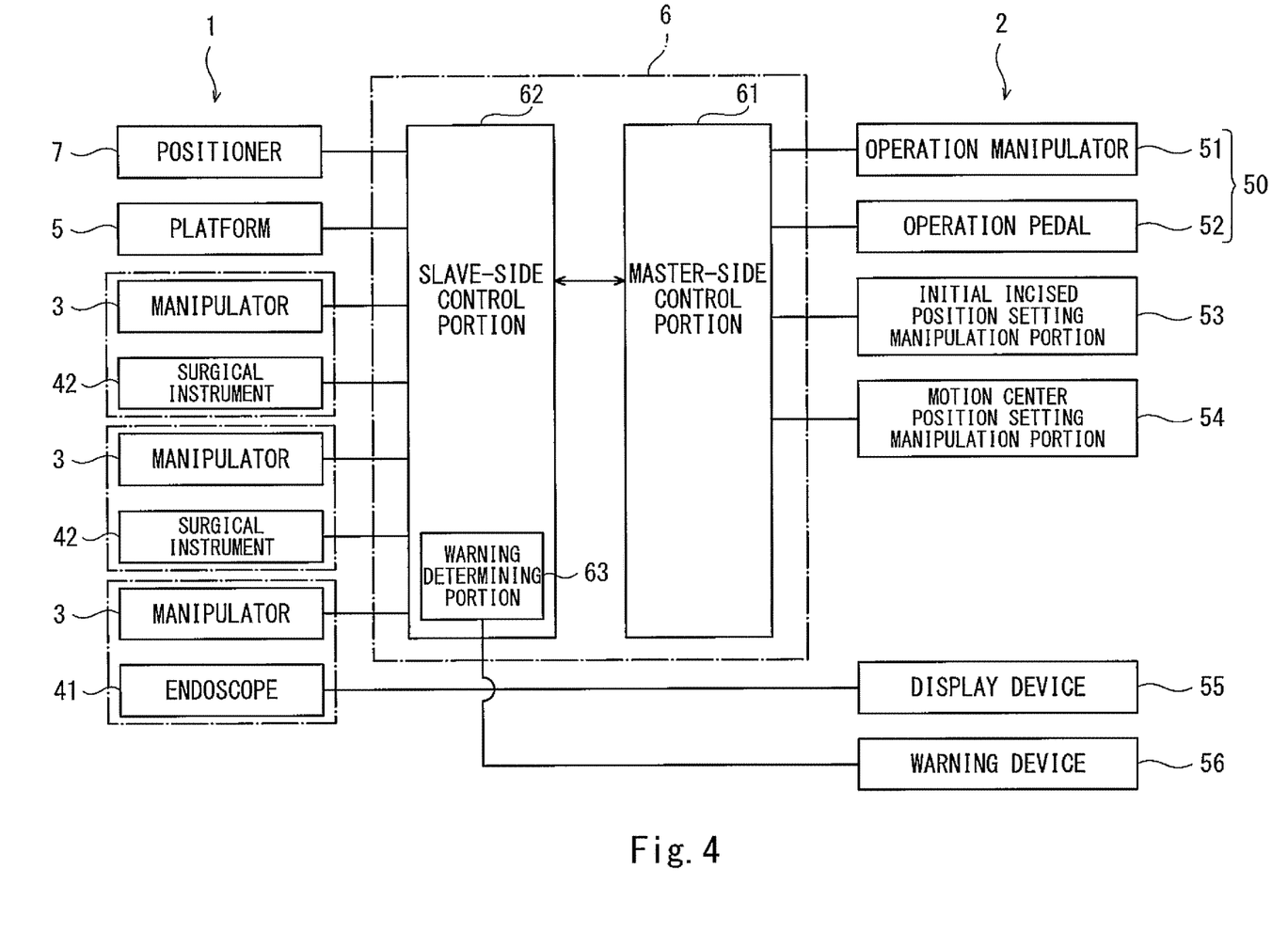
FIG. 4 is a block diagram showing a schematic configuration of the surgical system.

FIG. 1 is a schematic diagram showing one example of an entire configuration of a surgical system according to an embodiment of the present invention. FIG. 2 is a side view showing one example of the configuration of a positioner of a patient-side apparatus. FIG. 3 is a schematic diagram showing one example of the configuration of a manipulator (arm) to which a surgical instrument of the patient-side apparatus is attached. FIG. 4 is a block diagram showing a schematic configuration of the surgical system.

As shown in FIG. 1, a surgical system 100 is a system by which an operator O, such as a doctor, performs an endoscope surgery for a patient Q by using a manipulating apparatus 2 to manipulate a patient-side apparatus 1, like a robot assisted surgery, a robot remote surgery, etc.

The surgical system 100 includes the patient-side apparatus 1, the manipulating apparatus 2, and a control apparatus 6. The manipulating apparatus 2 is arranged away from the patient-side apparatus 1, and the patient-side apparatus 1 is remotely controlled by the manipulating apparatus 2. When the operator O manipulates the manipulating apparatus 2 in accordance with an operation to be performed by the patient-side apparatus 1, the manipulating apparatus 2 transmits to the control apparatus 6 a manipulate signal corresponding to the manipulation. The control apparatus 6 receives the manipulate signal transmitted from the manipulating apparatus 2 and operates the patient-side apparatus 1 based on the manipulate signal. Hereinafter, respective components of the surgical system 100 will be explained in detail.

Manipulating Apparatus

The manipulating apparatus 2 constitutes an interface between the surgical system 100 and the operator O and is an apparatus configured to manipulate the patient-side apparatus 1. The manipulating apparatus 2 is provided beside an operating table 111 in an operating room, away from the operating table 111, or outside the operating room.

The manipulating apparatus 2 includes: a manipulation input portion 50 to which the operator O inputs a manipulation command; and a display device 55 configured to display an image taken by an endoscope 41. The manipulation input portion 50 includes an operation manipulator 51, an operation pedal 52, and the like. While visually confirming an affected part on the display device 55, the operator O manipulates the manipulation input portion 50 to input the manipulation command to the manipulating apparatus 2. The manipulation command input to the manipulating apparatus 2 is transferred as the manipulate signal to the control apparatus 6 through a wire or wirelessly. Further, as shown in FIG. 4, the manipulating apparatus 2 includes an initial incised position setting manipulation portion (initial incised position setting portion) 53, a motion center position setting manipulation portion (motion center position setting portion) 54, and a warning device 56, which will be described later.

Patient-side Apparatus

The patient-side apparatus 1 constitutes an interface between the surgical system 100 and the patient Q. The patient-side apparatus 1 is arranged beside the operating table 111 on which the patient Q lies in the operating room.

The patient-side apparatus 1 includes: a positioner 7; a platform 5 attached to a tip end portion of the positioner 7; a plurality of patient-side manipulators 3 (hereinafter referred to as "arms 3") detachably attached to the platform 5; the endoscope 41 attached to a tip end portion of an arm 3A that is one of the plurality of arms 3; and surgical instruments 42 (hereinafter referred to as "instruments 42") detachably attached to tip end portions of arms 3B that are the remaining ones of the plurality of arms 3. The positioner 7 and the platform 5 are covered with a sterile drape 9. The patient-side apparatus 1 includes, for example, four arms 3 that are one arm 3A to which the endoscope 41 is attached and three arms 3B to which the respective instruments 42 are attached. It should be noted that FIG. 4 shows only three arms 3.

As shown in FIG. 2, the positioner 7 is basically a horizontal articulated robot and includes: a base 70 placed on a floor of the operating room; a lifting shaft 72; a swinging arm 71 coupling the base 70 and a base end portion of the lifting shaft 72; and a horizontal arm 73 coupled to a tip end portion of the lifting shaft 72. The platform 5 is coupled to a tip end portion of the horizontal arm 73.

The base 70 is, for example, a brake-equipped cart. The base 70 can be moved to a desired position and stopped thereat. A base end portion of the swinging arm 71 is coupled to the base 70 through a rotational joint J71. By the operation of the rotational joint J71, the swinging arm 71 rotates (swings) about a horizontal rotation axis defined at the base 70. The base end portion of the lifting shaft 72 is coupled to a tip end portion of the swinging arm 71 through a rotational joint J72. When the state of the swinging arm 71 changes from a vertically standing state shown in FIG. 2 to an inclined state by the operation of the rotational joint J71, a vertical state of the lifting shaft 72 is maintained by the operation of the rotational joint J72.

The lifting shaft 72 includes: a tubular member 72a; a hollow shaft member 72b inserted into the tubular member 72a so as to be able to advance and retreat in a vertical direction; and a translational joint J73 coupling these members (72a and 72b). By the operation of the translational joint J73, the shaft member 72b advances and retreats relative to the tubular member 72a in the vertical direction. Thus, the lifting shaft 72 can expand and contract in the vertical direction.

The horizontal arm 73 includes: first and second links 74 and 75 extending horizontally; and a wrist link 76 coupled to a tip end portion of the second link 75. The platform 5 is connected to a tip end portion of the wrist link 76.

A base end portion of the first link 74 is coupled to a tip end portion of the lifting shaft 72 through a rotational joint J74. By the operation of the rotational joint J74, the first link 74 rotates about a vertical rotation axis defined at the tip end portion of the lifting shaft 72. A tip end portion of the first link 74 is coupled to a base end portion of the second link 75 through a rotational joint J75. By the operation of the rotational joint J75, the second link 75 rotates about a vertical rotation axis defined at the tip end portion of the first link 74.

A tip end portion of the second link 75 is coupled to a base end portion of the wrist link 76 through a rotational joint J76. By the operation of the rotational joint J76, the wrist link 76 rotates about a horizontal rotation axis defined at the tip end portion of the second link 75. The wrist link 76 in a steady state extends vertically, and the platform 5 connected to the tip end portion of the wrist link 76 is held in a horizontal posture.

The platform 5 serves as a "hub" that is a base of the plurality of arm 3. The arms 3 are detachably attached to the platform 5. The arms 3 can be detached from the platform 5 and subjected to a cleaning treatment and a sterilization treatment.

In the present example, the positioner 7 and the platform 5 constitute an arm support S movably supporting the plurality of arms 3. It should be noted that the arm support S is only required to include at least the platform 5. The arm support S may be constituted by the platform 5 supported by a linear motion rail, a lifting device, a bracket attached to a ceiling or a wall, or the like instead of the positioner 7.

Next, one example of the configuration of the arm 3 will be explained. The plurality of arms 3 may be different in configuration from one another. Individual identification information is given to each arm 3.

FIG. 3 shows a schematic configuration of one of the plurality of arms 3 included in the patient-side apparatus 1. As shown in FIG. 3, the arm 3 includes: a first arm portion 30; and a second arm portion 35 coupled to a tip end portion of the first arm portion 30. The arm 3 is configured such that a tip end portion thereof can move relative to a base end portion thereof in a three-dimensional space. The arm 3 is configured such that, for example, the tip end portion thereof has six degrees of freedom in terms of the position and posture thereof.

The first arm portion 30 includes: a base 80 detachably attached to the platform 5; and first to sixth links 81 to 86 sequentially coupled to one another from the base 80 to the tip end portion. More specifically, a base end portion of the first link 81 is coupled to a tip end portion of the base 80 through a twisting joint J31. A base end portion of the second link 82 is coupled to a tip end portion of the first link 81 through a twisting joint J32. A base end portion of the third link 83 is coupled to a tip end portion of the second link 82 through a bending joint J33. A base end portion of the fourth link 84 is coupled to a tip end portion of the third link 83 through a twisting joint J34. A base end portion of the fifth link 85 is coupled to a tip end portion of the fourth link 84 through a bending joint J35. A base end portion of the sixth link 86 is coupled to a tip end portion of the fifth link 85 through a twisting joint J36. A base end portion (base end-side link 91) of the second arm portion 35 is coupled to a tip end portion 30a of the sixth link 86.

The second arm portion 35 includes the base end-side link 91 and a tip end-side link 92. The base end-side link 91 is attached to the tip end portion 30a of the sixth link 86 so as to be rotatable about a first axis L1. The tip end-side link 92 is attached to a tip end portion of the base end-side link 91 through a coupling portion 93 so as to be rotatable about a second axis L2. A rotating shaft 94 is attached to a tip end portion of the tip end-side link 92 so as to be rotatable about a third axis L3. A holder 36 is fixed to the rotating shaft 94. The instrument 42 is attached to the holder 36 so as to be easily detachable from the holder 36.

The second arm portion 35 is a mechanism configured to translate the holder 36, attached to the tip end portion of the second arm portion 35, in a reference direction D to translate the instrument 42, attached to the holder 36, in an extending direction (reference direction D) of a shaft 43 of the instrument 42.

To be specific, the second arm portion 35 is configured to be able to move the holder 36 relative to the tip end portion 30a of the first arm portion 30 in the extending direction of the shaft 43 without changing the posture of the holder 36. The second arm portion 35 may be connected to the first arm portion 30 and the holder 36 through respective rotational joints, and the base end-side link 91 and the tip end-side link 92 may also be connected to each other through a rotational joint. It should be noted that the holder 36 may be moved in the extending direction of the shaft 43 without changing the posture of the holder 36 by using a translational joint instead of the second arm portion 35.

The first arm portion 30 is configured such that the tip end portion 30a thereof has, for example, six degrees of freedom in terms of the position and posture thereof. The second arm portion 35 is coupled to the tip end portion 30a of the first arm portion 30.

According to the above configuration, the position and posture of the instrument 42 attached to the holder 36 can be freely changed in a three-dimensional space by the operation of the arm 3.

It should be noted that the patient-side apparatus 1 is not limited to the above arm support S and arms 3. The patient-side apparatus 1 is only required to include a manipulator which can freely change the position and posture of the instrument 42 attached to the tip end of the manipulator by the manipulation of the manipulating apparatus 2.

The instrument 42 includes: a drive unit 45 provided at a base end portion of the instrument 42; an end effector (treatment tool) 44 provided at a tip end portion of the instrument 42; and the long and thin rod-shaped shaft 43 connecting the drive unit 45 and the end effector 44. The instrument 42 is attached to the holder 36 such that the extending direction of the shaft 43 coincides with the reference direction D. The end effector 44 of the instrument 42 is selected from the group consisting of: tools including operating joints (such as forceps, scissors, a grasper, a needle holder, a microdissector, a staple applier, a tucker, a suction cleaning tool, a snare wire, and a clip applier); and tools not including joints (such as a cutting blade, a cautery probe, a cleaning tool, a catheter, and a suction orifice).

Further, regarding the arm 3 (3A) to which the endoscope 41 is attached, the endoscope 41 instead of the instrument 42 is detachably held by the holder 36. It should be noted that the holder 36 to which the endoscope 41 is attached may be different in aspect from the holder 36 to which the instrument 42 is attached.

The platform 5 is configured such that a plurality of arms 3 can be attached to each of a side surface and lower surface of the platform 5. The base 80 of the arm 3 includes an interface portion 801 (hereinafter referred to as an "I/F portion 801"), and the I/F portion 801 is connected to an attachment port (not shown) of the platform 5. The I/F portion 801 includes a connector for an electric wire or a communication wire, and the connector is connected to a socket provided at the attachment port of the platform 5. Further, the I/F portion 801 includes an IC tag storing, for example, the individual identification information of the arm 3. Then, the platform 5 includes a tag reader/writer configured to read the information of the IC tag and output the information to the control apparatus 6. For example, the control apparatus 6 can determined based on the individual identification information of the arm 3 whether or not the arm 3 is appropriate for the surgery performed based on surgery information input from the manipulating apparatus 2.

Control Apparatus

As shown in FIG. 4, the control apparatus 6 includes a master-side control portion 61 and a slave-side control portion 62. For example, each of the master-side control portion 61 and the slave-side control portion 62 includes: a calculating portion, such as a CPU; a storage portion, such as a ROM and/or a RAM, storing an execution program of the CPU and various data; and the like.

Each of the joints of the positioner 7, the arms 3, and the like is configured to include: a servo motor; an encoder configured to detect a rotational position of the servo motor; and the like. The rotational position detected by the encoder is input to the slave-side control portion 62 of the control apparatus 6.

When the operator O manipulates the manipulation input portion 50 of the manipulating apparatus 2, the manipulate signal that is the manipulation command is input from the manipulation input portion 50 to the master-side control portion 61. When the manipulate signal is, for example, a signal regarding the position and posture of the instrument 42, the master-side control portion 61 calculates a command value of the position and posture of the instrument 42 based on the manipulate signal in accordance with, for example, kinematics computation. Then, the master-side control portion 61 outputs the command value of the position and posture to the slave-side control portion 62. In accordance with, for example, inverse kinematics computation, the slave-side control portion 62 calculates driving amounts of the joints of the arm 3 which amounts are necessary to make the position and posture of the instrument 42 coincide with the command value. Then, the slave-side control portion 62 drives the joints of the arms 3 based on the calculated driving amounts.

Further, when the manipulate signal from the manipulation input portion 50 is a signal regarding the operation (such as a holding operation of the forceps) of the end effector 44 of the instrument 42, the master-side control portion 61 calculates the command value of the driving amount of the end effector 44 based on the manipulate signal and outputs the command value to the slave-side control portion 62. The slave-side control portion 62 drives (operates) the end effector 44 based on the command value of the driving amount of the end effector 44.

Similarly, as to the positioner 7, when the manipulate signal from the manipulation input portion 50 is a signal regarding the position and posture of the platform 5, the master-side control portion 61 calculates the command value of the position and posture of the platform 5 based on the manipulate signal and outputs the command value of the position and posture to the slave-side control portion 62. The slave-side control portion 62 calculates the driving amounts of the joints of the positioner 7 which amounts are necessary to make the position and posture of the platform 5 coincide with the command value. Then, the slave-side control portion 62 drives the joints of the positioner 7 based on the calculated driving amounts.

Next, an outline of a procedure of performing surgery by using the surgical system 100 configured as above will be explained.

First, for example, an assistant operator incises a plurality of predetermined positions of a body surface of the patient Q on the operating table 111 and attaches cannulas 110 to the respective incised parts.

Then, the operator O manipulates the manipulating apparatus 2 to operate the positioner 7, and with this, position the platform 5 such that a positional relation between the platform 5 and the patient Q on the operating table 111 becomes a desired positional relation.

Next, for example, the operator O manipulates the manipulating apparatus 2 to (i) operate the arms 3 such that positional relations between the cannula 110 attached to the body surface of the patient Q and the endoscope 41 and between each cannula 110 and each instrument 42 become desired initial positional relations, and (ii) insert the endoscope 41 and the instruments 42 into the cannulas 110 and position the endoscope 41 and the instruments 42 (positioning step).

Then, with the positioner 7 basically in a stationary state, the arms 3 are operated in accordance with the manipulate signal from the manipulating apparatus 2. Thus, the medical treatment is performed by operating the end effectors 44 of the instruments 42 while suitably displacing the endoscope 41 and the instruments 42 and changing the postures of the endoscope 41 and the instruments 42.

In the present embodiment, when the instrument 42 is first inserted into the cannula 110 and positioned in the positioning step, as shown in FIGS. 5A to 5D, an initial position (initial incised position P1) of an incised part Q1 of the patient Q into which the instrument 42 is inserted and a motion center position P2 that is a center point of an operation (motion), such as turning, of the instrument 42 during the medical treatment are set (stored) in the control apparatus 6. Therefore, as shown in FIG. 4, the manipulating apparatus 2 includes: the initial incised position setting manipulation portion 53 as a manipulation portion configured to set the initial incised position P1; and the motion center position setting manipulation portion 54 as a manipulation portion configured to set the motion center position P2. Each of these manipulation portions 53 and 54 can be configured by a push button switch, or the like.

FIGS. 5A to 5D are diagrams showing one example of a procedure of setting the initial incised position P1 and the motion center position P2.

Figure 5A:
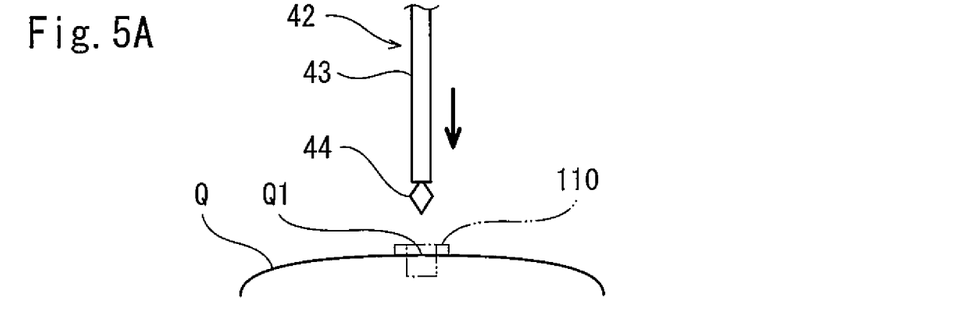
FIGS. 5A to 5D are diagrams for explaining one example of a method of setting an initial incised position and a motion center position.
Figure 5B:
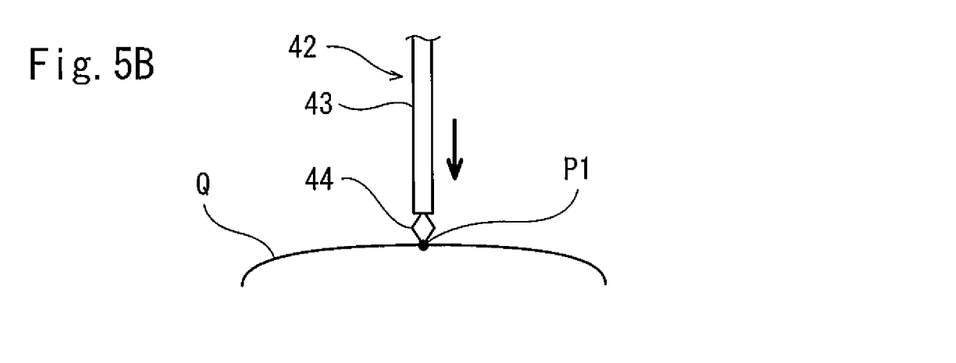

As shown in FIG. 5A, the operator O manipulates the manipulating apparatus 2 to make the instrument 42 approach the cannula 110 attached to the incised part Q1 of the patient Q. Then, as shown in FIG. 5B, when the tip end of the instrument 42 is located at a position on the body surface of the incised part Q1, the operator O manipulates the initial incised position setting manipulation portion 53 to set the position of the tip end of the instrument 42 as the initial incised position P1. It should be noted that in FIGS. 5B to 5C, the cannula 110 is omitted.

Figure 5C:
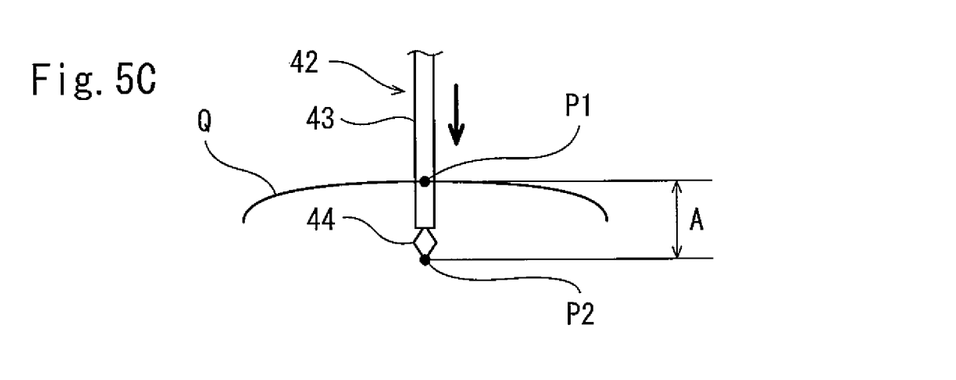
Figure 5D:
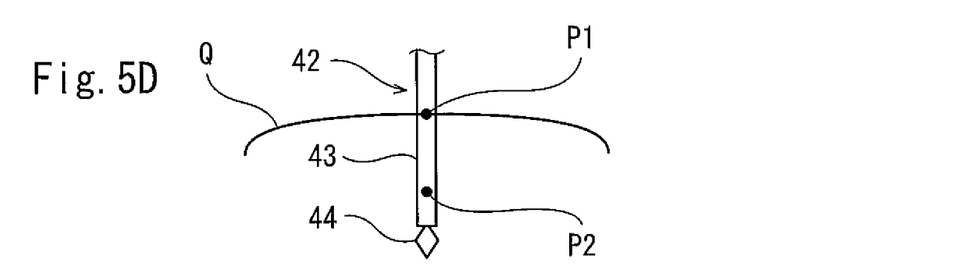

Then, as shown in FIG. 5C, the instrument 42 is further moved in an axial direction (extending direction) of the shaft 43. When the operator O determines that the tip end of the instrument 42 is located at a desired motion center position, the operator O manipulates the motion center position setting manipulation portion 54 to set the position of the tip end of the instrument 42 as the motion center position P2. Then, as shown in FIG. 5D, the instrument 42 is further moved in the axial direction of the shaft 43 such that the tip end of the instrument 42 is inserted to a desired initial position. Thus, the shaft 43 is arranged so as to pass through the initial incised position P1 and the motion center position P2.

Similarly, the tip ends of the other instruments 42 and the tip end of the endoscope 41 are inserted through the corresponding cannulas 110 into the body to the corresponding desired initial positions. Then, the medical treatment is practically started.

In the example shown in FIGS. 5A to 5D, by the manipulation of the initial incised position setting manipulation portion 53, the position of the tip end of the instrument 42 at the time of this manipulation is set as the initial incised position P1. Further, by the manipulation of the motion center position setting manipulation portion 54, the position of the tip end of the instrument 42 at the time of this manipulation is set as the motion center position P2.

It should be noted that when the initial incised position P1 is set as shown in FIG. 5B, the motion center position P2 may be automatically set by being calculated as a position away from the initial incised position P1 by a predetermined distance (A) in the axial direction of the instrument 42 (i.e., the axial direction of the shaft 43).

These positions P1 and P2 are stored in, for example, the slave-side control portion 62 of the control apparatus 6 by using three-dimensional position coordinates. The three-dimensional position coordinates of the positions P1 and P2 can be calculated from: three-dimensional position coordinates of a reference position Ps1 (see FIG. 3) of the base end of the arm 3 to which the instrument 42 is attached; rotational positions (output values of the encoders) of the joints of the arm 3; lengths of the links constituting the arm 3; a length from the holder 36 to the tip end of the instrument 42; and the like. It should be noted that the three-dimensional position coordinates of the reference position Ps1 of the base end of the arm 3 may be calculated by using a three-dimensional orthogonal coordinate having an origin that is a predetermined position of the base 70 of the positioner 7. Further, in this example, after the platform 5 is first positioned, the platform 5 is in a fixed state. Therefore, as to each arm 3, the three-dimensional position coordinates of the reference position (Ps1, for example) of the base end of the arm 3 may be regarded as the origin.

When the medial treatment is practically started, the operator O manipulates the manipulating apparatus 2 to change the position and posture of the instrument 42. At this time, the slave-side control portion 62 of the control apparatus 6 controls the operation of the arm 3 such that the position and posture of the instrument 42 are changed while maintaining a state where the shaft 43 of the instrument 42 is located at the motion center position P2. With this, the position and posture of the tip end of the instrument 42 are changed while maintaining a state where the shaft 43 passes through the motion center position P2.

As above, the motion center position P2 of the instrument 42 is set in (an inner part of) the body of the patient, instead of on the body surface of the patient or near the body surface of the patient. With this, even when the instrument 42 is inserted into a narrow region, for example, a region between bones, such as ribs, in thoracic surgery or the like, a large movable range of the tip end of the instrument 42 can be secured.

Figure 6A:
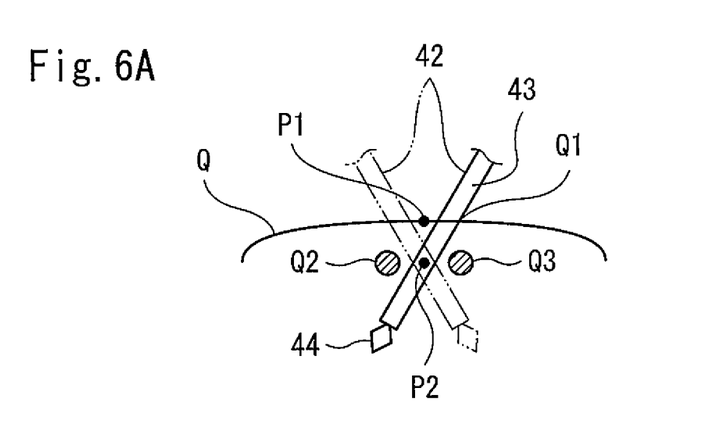
FIGS. 6A and 6B are diagrams for explaining an effect of the surgical system according to the present embodiment.
Figure 6B:
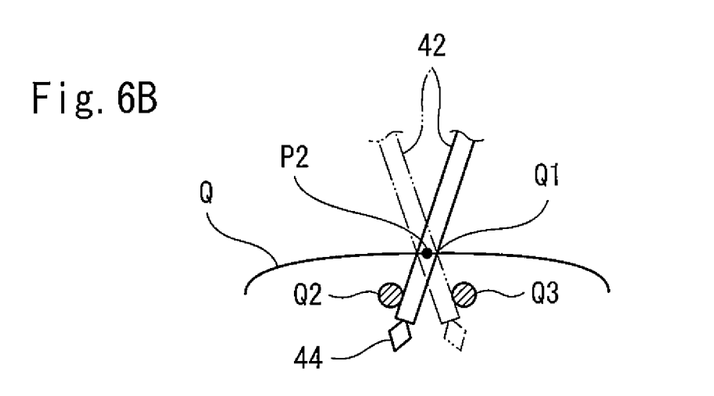

This will be explained with reference to FIGS. 6A and 6B. FIG. 6A is a diagram showing an operating state of the instrument 42 in one example of the present embodiment. FIG. 6B is a diagram showing an operating state of the instrument 42 in Comparative Example. It should be noted that in FIGS. 6A and 6B, the cannula 110 (see FIG. 5A) attached to the incised part Q1 is omitted.

According to the present embodiment shown in FIG. 6A, the motion center position P2 of the instrument 42 is set between bones Q2 and Q3 in the inner part of the body of the patient Q. According to Comparative Example shown in FIG. 6B, the motion center position P2 of the instrument 42 is set at a position of the incised part Q1 on the body surface of the patient Q.

As is clear from a comparison between FIGS. 6A and 6B, according to Comparative Example shown in FIG. 6B, in order to move the instrument 42 such that the instrument 42 does not contact the bones Q2 and Q3, the movable range of the end effector 44 of the tip end of the instrument 42 becomes small. However, according to the present embodiment shown in FIG. 6A, the large movable range of the end effector 44 of the tip end of the instrument 42 can be secured, and therefore, the surgery is easily performed.

In contrast, as in the present embodiment, when the instrument 42 is set such that the shaft 43 passes through the motion center position P2 set in the inner part of the body and moves about the motion center position P2, the position of the shaft 43 on the body surface is displaced from the initial incised position P1, and the cannula 110 into which the shaft 43 is inserted and the incised part Q1 of the patient Q are displaced from the initial incised position P1. When the incised part Q1 is displaced from the initial incised position P1, the periphery of the incised part Q1 is pulled or oppressed. Therefore, the increase in the degree of displacement is not preferable for the patient Q.

Therefore, according to the present embodiment, the manipulating apparatus 2 includes the warning device 56 (see FIG. 4) configured to output a warning to the operator O when the incised part Q1 is largely displaced from the initial incised position P1.

The slave-side control portion 62 of the control apparatus 6 includes a warning determining portion 63 configured to determine based on a predetermined warning determination condition whether to output the warning from the warning device 56. When the warning determining portion 63 determines that the warning is output, the warning determining portion 63 outputs a warning signal to the warning device 56. When the warning signal is input to the warning device 56, the warning device 56 outputs the warning. The warning device 56 warns the operator O by at least one of sound, light, and an image. The warning device 56 may be a buzzer, a unit configured to generate voice by electronic sound, or a light emitting unit, such as a lamp. Further, the display device 55 may be used as the warning device 56, and a warning image (such as letters, signals, etc. indicating the waning) may be displayed on the screen image of the display device 55.

Figure 7A:
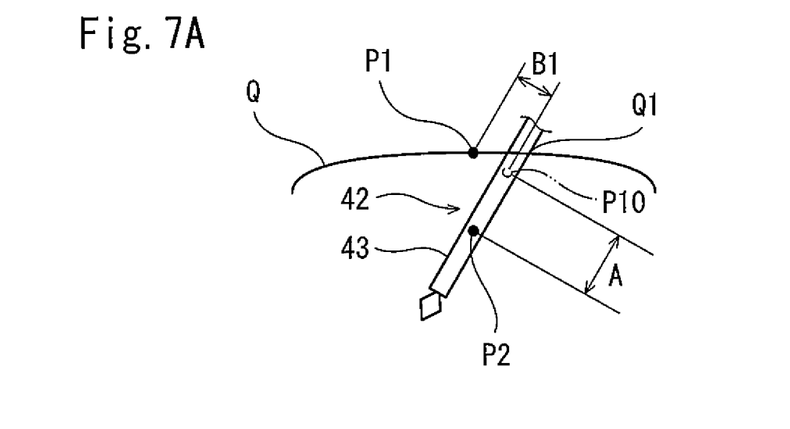
FIGS. 7A, 7B, and 7C are diagrams for explaining a warning determination condition.
Figure 7B:
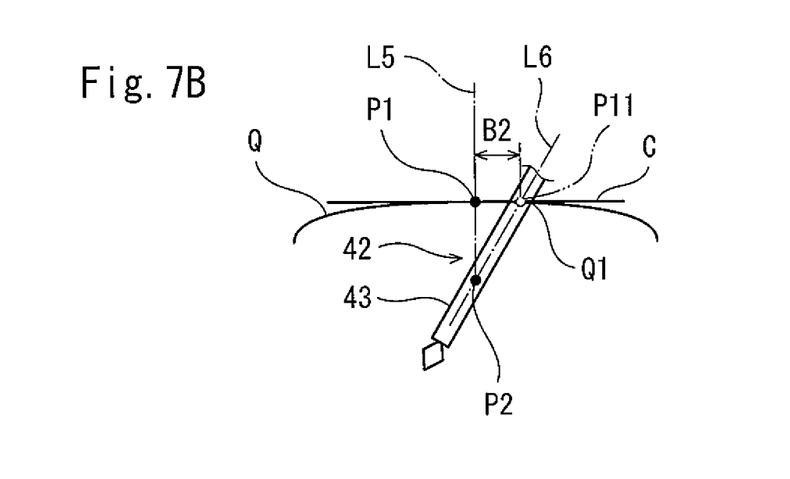
Figure 7C:
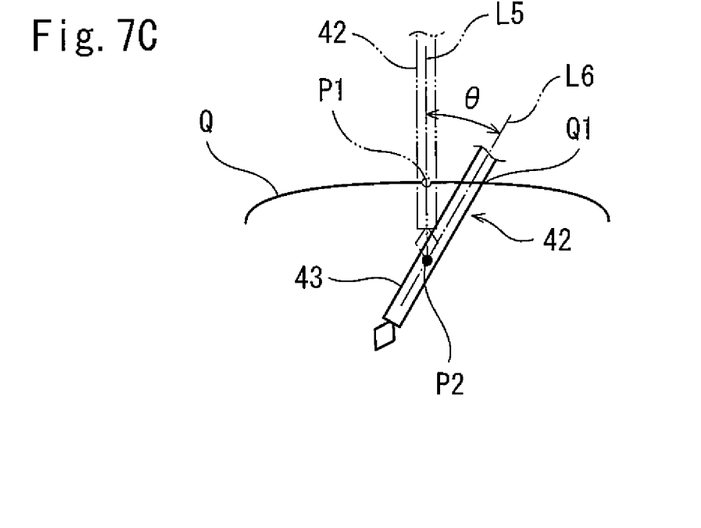

FIGS. 7A, 7B, and 7C are diagrams for explaining the warning determination condition in the warning determining portion 63. It should be noted that in FIGS. 7A to 7C, the cannula 110 (see FIG. 5A) attached to the incised part Q1 is omitted. Further, as described above, the three-dimensional position coordinates of the initial incised position P1 and the motion center position P2 are stored in the slave-side control portion 62.

In FIG. 7A, the warning determining portion 63 sets a distance between the initial incised position P1 and the motion center position P2 (also see FIG. 5C) as a distance A and calculates a position P10 located on a central axis of the current shaft 43 and away from the motion center position P2 toward the base end of the shaft 43 by the distance A. Then, the warning determining portion 63 calculates a distance B1 between the position P10 and the initial incised position P1 at all times. When the distance B1 is not less than a predetermined value, the warning determining portion 63 determines that the warning is output. Then, the warning determining portion 63 outputs the warning signal.

In FIG. 7B, the warning determining portion 63 obtains a flat plane C perpendicular to a vector (vector parallel to a straight line L5) passing through the initial incised position P1 and extending from the motion center position P2 toward the initial incised position P1. Then, the warning determining portion 63 calculates a distance B2 between a position P11 where the flat plane C and a central axis L6 of the current shaft 43 intersect with each other and the initial incised position P1 at all times. When the distance B2 is not less than a predetermined value, the warning determining portion 63 determines that the warning is output. Then, the warning determining portion 63 outputs the warning signal.

It is preferable that the flat plane C be a flat plane passing through the initial incised position P1 substantially along the body surface of the patient Q. For example, when the straight line L5 passing through the initial incised position P1 and the motion center position P2 is largely inclined from a vertical line, the flat plane C may be a horizontal surface passing through the initial incised position P1.

It can be said that each of the calculation of the distance B1 in FIG. 7A and the calculation of the distance B2 in FIG. 7B is a calculation of an approximate value or rough value of a distance between the center position of the current incised part Q1 (i.e., the incised part Q1 at the time of the calculation) and the initial incised position P1. To be specific, it can also be said that the warning determination condition in each of FIGS. 7A and 7B is a condition in which the approximate value or rough value (distance B1, B2) of the distance between the center position of the current incised part Q1 and the initial incised position P1 is not less than the predetermined value.

In FIG. 7C, the warning determining portion 63 calculates at all times an angle $\theta$ formed by a direction of the central axis (straight line L5) of the shaft 43 when the motion center position P2 is set and a direction of the central axis L6 of the current shaft 43. When the angle $\theta$ is not less than a predetermined angle, the warning determining portion 63 determines that the warning is output. Then, the warning determining portion 63 outputs the warning signal. The warning determination condition in this case is a condition in which the angle θ is not less than the predetermined angle.

It should be noted that the angle θ can be calculated by using: information (first vector) of the direction of the central axis (straight line L5) of the shaft 43 when the motion center position P2 is set; information (second vector) of the direction of the central axis L6 of the current shaft 43; and an inner product of these vectors. Since the central axis of the shaft 43 passes through the motion center position P2 at all times, the vector (first or second vector) indicating the direction of the central axis of the shaft 43 at an arbitrary point of time can be calculated from: the motion center position P2; and a reference position Ps2 (see FIG. 3) of the base end of the shaft 43 at the arbitrary point of time. Further, the reference position Ps2 of the base end of the shaft 43 can be calculated from: the three-dimensional position coordinates of the reference position Ps1 of the base end of the arm 3; the rotational positions (output values of the encoders) of the joints of the arm 3; lengths of the links constituting the arm 3; and the like.

In FIG. 7C, since the angle θ can be obtained without using the three-dimensional position coordinates of the initial incised position P1, the initial incised position P1 does not have to be set.

It should be noted that the warning determining portion 63 is only required to perform the determination based on the warning determination condition explained in any one of FIGS. 7A, 7B, and 7C.

In the foregoing, the operator O manipulates the manipulating apparatus 2 to move the arm 3. Then, when the position of the tip end of the instrument 42 is located at the initial incised position P1, the operator O manipulates the setting manipulation portion 53 to set the position P1, and when the position of the tip end of the instrument 42 is located at the desired motion center position P2, the operator O manipulates the setting manipulation portion 54 to set the position P2. In this case, a camera may be additionally provided to take an image of the body surface, to which the cannula 110 is attached, of the patient Q. The image taken by the camera may be displayed on the screen image of the display device 55, and the operator O may perform manipulation while watching the screen image.

Further, for example, like direct teaching of an industrial robot, the position P1 may be set when the position of the tip end of the instrument 42 is located at the initial incised position P1 after the arm 3 is directly moved by a hand of an assistant operator, and the position P2 may be set when the position of the tip end of the instrument 42 is located at the desired motion center position P2 after the arm 3 is directly moved by a hand of an assistant operator. In this case, the position P1 and the position P2 may be set by manipulating a remote controller having the function of the initial incised position setting manipulation portion 53 and the function of the motion center position setting manipulation portion 54.

Further, in the foregoing, the position of the tip end of the instrument 42 is set as the reference point, and the initial incised position P1 and the motion center position P2 are set by the position of the tip end of the instrument 42. However, the above embodiment is not limited to this. For example, a reference point may be provided in the vicinity of the tip end of the shaft 43 of the instrument 42, a mark (a colored mark, an engraved mark, or the like) of the reference point may be put on the shaft 43, and the initial incised position P1 and the motion center position P2 may be set by the position of the reference point.

Further, regarding the setting of the initial incised position P1, a special arm 3 having a tip end to which a probe for setting the initial incised position is attached may be used, and the initial incised position P1 may be set by the position of the tip end of the probe.

Further, regarding the setting of the initial incised position P1, a three-dimensional position sensor may be attached to the patient-side apparatus 1 and detect the position of the incised part Q1, and then, the detected position may be input to the control apparatus 6 and set as the initial incised position P1. In this case, coordinates of the position detected by the three-dimensional position sensor need to be converted into coordinates of the patient-side apparatus 1 and then set as the initial incised position P1.

When the initial incised position P1 is set by using the probe for setting the initial incised position or the three-dimensional position sensor, the motion center position P2 may be set as, for example, a position located away from the initial incised position P1 by a predetermined distance in a predetermined direction (for example, a vertically downward direction).

The present embodiment has explained an example in which the thoracic surgery is performed. However, the manipulating apparatus 2 may include a mode selecting portion configured to select a first operating mode used when thoracic surgery or the like is performed and a second operating mode used when abdominal surgery or the like is performed. When the first operating mode is selected, the motion center position P2 is set in the body, i.e., in the inner part under the body surface of the patient Q as described above. When the initial incised position P1 is necessary for the determination by the warning determining portion 63 as in FIGS. 7A and 7B, the initial incised position P1 is set at the position of the incised part Q1 on the body surface of the patient Q. In contrast, when the second operating mode is selected, the motion center position P2 is set at the position of the incised part Q1 on the body surface of the patient Q, and the function of setting the initial incised position P1 may be stopped. Further, when the second operating mode is selected, the function of the warning determining portion 63 is also stopped.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

INDUSTRIAL APPLICABILITY

The present invention is useful as, for example, a surgical system capable of securing a large movable range of a tip end of a surgical instrument even when the surgical instrument is inserted into a narrow region, for example, a region between bones, such as ribs.

REFERENCE SIGNS LIST 1 patient-side apparatus
2 manipulating apparatus
3 manipulator
6 control apparatus
42 surgical instrument
43 shaft
44 end effector (treatment tool)

50 manipulation input portion
53 initial incised position setting manipulation portion
54 motion center position setting manipulation portion
56 warning device
Q patient
Q1 incised part
Q2, Q3 bone
P1 initial incised position
P2 motion center position

The invention claimed is:

1. A surgical system comprising:
a manipulator including a tip end portion and a base end portion, the tip end portion being configured to move relative to the base end portion in a three-dimensional space;
a surgical instrument including:
  a rod-shaped shaft coupled to the tip end portion of the manipulator, and
  a treatment tool provided at a tip end portion of the shaft;
a manipulation input portion to which an operator inputs a command regarding a position and a posture of the surgical instrument;
a control apparatus configured to control an operation of the manipulator based on the inputted command; and
a motion center position setting portion configured to set a desired position in the control apparatus as a motion center position of the surgical instrument inserted into an incised part of a patient, the desired position being located in an inner part under a body surface of the patient and located separated away from the incised part of the patient by a predetermined distance, wherein the control apparatus is configured to control the operation of the manipulator such that in a case where the control apparatus controls the operation of the manipulator based on the inputted command after the surgical instrument is inserted into a body of the patient through the incised part, the surgical instrument being arranged with the shaft passing through the motion center position, and the position and the posture of the surgical instrument are changed while maintaining a state where the shaft is located at the motion center position.

2. The surgical system according to claim 1, wherein the motion center position setting portion includes a motion center position setting manipulation portion configured to perform an operation of setting the position as the motion center position in the control apparatus, when the surgical instrument is inserted into the body of the patient through the incised part, and a predetermined reference point of the surgical instrument is located at the desired position in the body.

3. The surgical system according to claim 1, further comprising:
an initial incised position setting portion configured to set a position of the incised part on the body surface of the patient as an initial incised position in the control apparatus; and
a warning device configured to output a warning to the operator when the shaft is displaced from the initial incised position, and a predetermined condition is satisfied in a case where the control apparatus controls the operation of the manipulator after the surgical instrument is inserted into the body of the patient through the incised part, and the surgical instrument is arranged with the shaft passing through the motion center position.

4. The surgical system according to claim 1, wherein the motion center position setting portion includes:
an initial incised position setting portion configured to set a position of the incised part on the body surface of the patient as an initial incised position in the control apparatus; and
a calculating portion configured to calculate a position located away from the initial incised position by the predetermined distance in a predetermined direction and set the position as the motion center position in the control apparatus.

5. The surgical system according to claim 4, further comprising a warning device configured to output a warning to the operator when the shaft is displaced from the initial incised position, and a predetermined condition is satisfied in a case where the control apparatus controls the operation of the manipulator after the surgical instrument is inserted into the body of the patient through the incised part, and the surgical instrument is arranged with the shaft passing through the motion center position.

6. The surgical system according to claim 3, wherein the predetermined condition is a condition in which a distance between the initial incised position and a position located away from the motion center position on a central axis of the current shaft by a distance between the initial incised position and the motion center position is equal to or greater than a predetermined value.

7. The surgical system according to claim 3, wherein the predetermined condition is a condition in which a distance between the initial incised position and an intersecting position is equal to or greater than a predetermined value, the intersecting position being calculated as a position where a central axis of the current shaft intersects with a flat plane perpendicular to a vector, the vector passing through the initial incised position and extending from the motion center position toward the initial incised position.

8. The surgical system according to claim 3, wherein the initial incised position setting portion includes an initial incised position setting manipulation portion configured to perform an operation of setting the position as the initial incised position in the control apparatus, when the surgical instrument is inserted into the body of the patient through the incised part, and a predetermined reference point of the surgical instrument is located at a position of the incised part on the body surface of the patient.

9. The surgical system according to claim 1, further comprising a warning device configured to output a warning to the operator when an angle formed by a vector indicating a direction of a central axis of the shaft when the motion center position is set and a vector indicating a direction of the central axis of the current shaft is equal to or greater than a predetermined angle in a case where the control apparatus controls the operation of the manipulator after the surgical instrument is inserted into the body of the patient through the incised part, and the surgical instrument is arranged with the shaft passing through the motion center position.

10. The surgical system according to claim 1, wherein the motion center position is defined between adjacent bones in the body of the patient.

* * * * *